US008697920B2

(12) United States Patent
Baudot et al.

(10) Patent No.: US 8,697,920 B2
(45) Date of Patent: Apr. 15, 2014

(54) USE OF SOLIDS BASED ON ZINC FERRITE IN A PROCESS FOR DEEP DESULPHURIZING OXYGEN-CONTAINING FEEDS

(75) Inventors: Arnaud Baudot, Vernaison (FR); Thierry Huard, Saint Symphorien D'Ozon (FR); Michel Thomas, Lyons (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 1223 days.

(21) Appl. No.: 12/576,675

(22) Filed: Oct. 9, 2009

(65) Prior Publication Data
US 2010/0089798 A1    Apr. 15, 2010

(30) Foreign Application Priority Data

Oct. 10, 2008  (FR) ...................................... 08 05624

(51) Int. Cl.
*C07C 7/12*    (2006.01)

(52) U.S. Cl.
USPC ............ 568/917; 568/913; 568/920; 585/820

(58) Field of Classification Search
USPC ......... 208/213, 217, 244, 247, 295, 296, 299, 208/300; 585/820; 568/913, 917, 920
See application file for complete search history.

(56) References Cited

U.S. PATENT DOCUMENTS

| 3,832,455 A * | 8/1974 | Smith et al. ................. 423/594.1 |
| 5,914,288 A | 6/1999 | Turk et al. |
| 6,290,734 B1 * | 9/2001 | Scott et al. ...................... 44/451 |

FOREIGN PATENT DOCUMENTS

WO    WO 01/70393 A1    9/2001

OTHER PUBLICATIONS

Search Report of FR 0805624 (May 28, 2009).

* cited by examiner

*Primary Examiner* — Renee E Robinson
(74) *Attorney, Agent, or Firm* — Millen, White, Zelano & Branigan, P.C.

(57) ABSTRACT

The invention concerns a process for desulphurizing a feed comprising oxygen-containing compounds, hydrocarbon-containing compounds and organic sulphur-containing compounds, by capturing sulphur on a capture mass comprising iron oxides or zinc oxides and more than 20% by weight of zinc ferrite. The process is operated in the presence of hydrogen at a temperature in the range 200° C. to 400° C.

16 Claims, No Drawings

USE OF SOLIDS BASED ON ZINC FERRITE IN A PROCESS FOR DEEP DESULPHURIZING OXYGEN-CONTAINING FEEDS

CROSS REFERENCE TO RELATED APPLICATION

This application is related to a concurrently filed application bearing U.S. application Ser. No. 12/576,680, entitled "USE OF ZINC FERRITE-BASED SOLIDS IN A PROCESS FOR DEEP DESULFURIZATION OF HYDROCARBON FRACTIONS" by Celine Babe et al., based on French Priority Application 08/05.623. The related application is incorporated by reference herein.

Feeds comprising oxygen-containing compounds can be brought into contact with a catalyst for the production of hydrogen by steam reforming, partial oxidation or autothermal reforming reactions. A complementary water gas shift reaction can increase the hydrogen yield significantly. The presence of impurities in the feed, in particular sulphur-containing impurities, is deleterious, however, as it results in gradual deactivation of the catalyst or catalysts used in such reactions.

Several processes are used to produce hydrogen from alcohol-rich feeds. Examples which may be cited are:

the partial oxidation reaction (POX), carried out with a controlled quantity of air, is exothermic, and when ethanol is used its chemical equation is written as follows:

$$CH_3-CH_2-OH + \tfrac{1}{2} O_2 \Rightarrow 2CO + 3H_2$$

the steam reforming reaction, which is endothermic, which is written as follows:

$$CH_3-CH_2-OH + H_2O \Rightarrow 2CO + 4H_2$$

the autothermal reforming reaction, which couples the above two reactions together, which may be considered to be generally adiabatic, the exothermicity of one reaction being approximately compensated for by the endothermicity of the other.

The synthesis gas obtained is thus primarily composed of carbon monoxide and hydrogen. It may also contain not simply nitrogen from the air, and excess steam, but also sulphur-containing compounds deriving from degradation of the sulphur-containing compounds initially present in the feed.

A complementary water gas shift reaction (WGS) can substantially increase the hydrogen yield by oxidation of the carbon monoxide of synthesis gas. This reaction is as follows:

$$CO + H_2O \Rightarrow CO_2 H_2$$

These chemical reactions are carried out in the gas phase, frequently at high temperature, typically more than 200° C., frequently more than 600° C., in the presence of catalysts, which are often highly sensitive to the presence of sulphur-containing compounds in the feed which may then result in their gradual deactivation.

The ultimate purification of hydrogen, for example after the water gas shift reaction, to obtain purities of more than 99.9%, may be carried out using a PSA (pressure swing adsorption) type adsorption process or by using a palladium-based metallic membrane. In all cases, the presence of sulphur-containing impurities, in particular hydrogen sulphide, is deleterious to these processes.

For legal reasons, denaturing agents are added to alcohol-rich feeds in order to render those feeds unsuitable for food consumption. The quantity of denaturing agents is generally in the range 1% to 10% by weight of the quantity of alcohol, more frequently in the range 2% to 5% by weight.

The denaturing agent may be a natural gas condensate or a gasoline, gas oil or naphtha type hydrocarbon cut. In addition to the hydrocarbon compounds, that denaturing agent generally comprises sulphur-containing compounds of the light or intermediate mercaptan type, or aromatic sulphur-containing compounds such as thiophene, benzothiophene or dibenzothiophene and their substituted derivatives. The sulphur equivalent in the feed is variable but it is generally less than 2000 ppmS, and usually less than 500 ppmS, or even 100 ppmS or even 50 ppmS.

The presence of said sulphur-containing compounds in the feed, even in small quantities, may prove to be deleterious to the correct function of the catalyst or catalysts following gradual deactivation due to poisoning. Further, deep purification of the hydrogen obtained, either using a PSA (pressure swing adsorption) type process or using a palladium-based membrane, may also prove to be highly problematic.

PRIOR ART

Many processes for desulphurizing liquid or gaseous feeds on solids have been described in the prior art.

Examples which can be cited are processes for desulphurizing natural gas, with the removal of light mercaptans in particular, using a molecular sieve generally of the NaX type (13X), under pressure, typically in the range 50 to 100 bar, with a thermal regeneration step at high temperature, generally of the order of 300° C. Patent application WO-03/062177 (A1) describes an example of that type of process.

Patent US-2005/0109206 describes in particular the use of a molecular sieve to remove mercaptans from natural gas with a regeneration method including, in particular, a step for displacement of the adsorbed mercaptans using a purge gas enriched with hydrocarbon compounds containing more than five carbon atoms.

Patent application US-2006/0131216 describes a process for desulphurizing hydrocarbon feeds, such as a natural gas, using a first solid carrying out the hydrolysis, in the presence of steam and a catalyst such as alumina, titanium, or zirconia, of sulphur-containing COS and $CS_2$ type compounds to other sulphur-containing compounds, in particular $H_2S$, which are subsequently captured by a second adsorbant solid, in particular of the zinc oxide or nickel oxide type.

Processes for desulphurizing liquid feeds, for example of the gas oil or gasoline type using adsorption or chemisorption type processes may also be cited.

Patent U.S. Pat. No. 3,620,969 describes, for example, the use of a molecular sieve to desulphurize liquid hydrocarbon cuts, with a step for thermal regeneration using a purge gas containing traces of moisture.

Patent application US-2007/261993A describes a process for desulphurizing gasolines derived from catalytic cracking (FCC), involving a step for distillation of the gasoline into a light fraction containing at least thiophene, and a heavy fraction, the light cut being desulphurized using a liquid phase adsorption process over a faujasite X type molecular sieve, the heavy cut being desulphurized by a conventional hydrotreatment process over a catalyst comprising at least one element from group VIII (element selected from the group constituted by chromium, molybdenum and tungsten), at least partially in the sulphide form.

Patent U.S. Pat. No. 5,882,614 describes the use of solids such as zinc oxide and metallic nickel to desulphurize a natural gas containing sulphur-containing impurities in particular such as H₂S, COS and light mercaptans, prior to its transformation into synthesis gas.

Patent U.S. Pat. No. 6,159,256 describes a method for desulphurizing a hydrocarbon feed using a nickel-based catalyst to obtain a purified effluent, the sulphur having reacted with the nickel to form nickel sulphide.

Patent U.S. Pat. No. 6,428,685 describes a process for desulphurizing hydrocarbon cuts, in particular gasolines or gas oils, using a metallic promoter based on copper, cobalt, nickel, manganese coupled with a calcium salt (sulphate, silicate, phosphate, aluminate).

Patent application US-2004/0091753 describes a process for desulphurizing a hydrocarbon feed intended for the production of hydrogen, by adsorption of sulphur-containing compounds onto a first solid operating at moderate temperature, of the zeolite, coal, activated alumina, clay, silica-alumina type, then on a nickel-based solid operating at high temperature.

Patent application US-2003/0163013 describes the use of microporous solids such as Y zeolites exchanged with transition metal cations (Cu, Ag), to carry out the desulphurization of liquid hydrocarbon cuts such as a gasoline via the π-complexing phenomenon.

Patent application US-2003/0183803 claims the use of oxide of copper and a reduced metallic promoter to carry out the desulphurization of hydrocarbon feeds.

Finally, patent application US-2002/0139718 A1 claims a process for desulphurizing liquid hydrocarbon feeds such as gasoline or gas oils using nickel in the presence of an oxygen-containing effluent such as methanol, ethanol or MTBE.

BRIEF DESCRIPTION OF THE INVENTION

The invention concerns a process for desulphurizing a feed comprising oxygen-containing compounds, hydrocarbon-containing compounds and organic sulphur-containing compounds, by capturing sulphur on a capture mass comprising iron oxides or zinc oxides and more than 20% by weight of zinc ferrite.

DETAILED DESCRIPTION OF THE INVENTION

The invention concerns a process for desulphurizing a feed comprising oxygen-containing compounds, preferably methanol and/or ethanol, hydrocarbon-containing compounds and organic sulphur-containing compounds, preferably aliphatic, cyclic and/or aromatic sulphur-containing compounds, by capturing sulphur on a capture mass comprising iron oxides or zinc oxides and more than 20% by weight of zinc ferrite. The process is operated in the presence of hydrogen at a temperature in the range 200° C. to 400° C.

The capture mass comprises more than 20% by weight of zinc ferrite, more preferably more than 50% by weight of zinc ferrite, and more preferably more than 80% by weight of zinc ferrite, still more preferably more than 98% by weight of zinc ferrite, and still more preferably more than 99.5% by weight of zinc ferrite.

The pressure is generally in the range 0.2 to 3.5 MPa, preferably in the range 0.5 to 3 MPa, and still more preferably in the range 0.5 to 1.5 MPa. The hourly space velocity of the feed to be treated is generally in the range $0.1\ h^{-1}$ to $10\ h^{-1}$, preferably in the range $0.5\ h^{-1}$ to $5\ h^{-1}$. The hourly space velocity, HSV, of the treated liquid feed is defined as the volume flow rate of the treated liquid feed over the volume of the solid compound. The hydrogen/feed volume ratio is generally in the range 5 to 500, preferably in the range 50 to 300.

The flow rates of the hydrogen and of the liquid feed to be treated are given under normal conditions.

The process of the invention can reduce the sulphur content of the feed and limit the phenomena of deactivation of the catalyst or catalysts used in the successive hydrogen production reactions.

The sulphur present in these feeds essentially derives from denaturing agents of the natural gas condensate, gasoline, naphtha, gas oil or any hydrocarbon cut type comprising sulphur-containing compounds. The quantity of denaturing agent in the feed comprising the oxygen-containing compounds is generally in the range 1% to 10% by weight, more frequently in the range 1% to 5% or 1% to 2% by weight. The sulphur content in said denaturing agent is in the range 1 to 5000 ppm sulphur equivalent, and more generally in the range 10 to 500 ppmS, or even in the range 10 to 100 ppmS.

Depending on the nature of the denaturing agent, the nature of the sulphur-containing compounds can vary. In the case of a natural gas condensate, they are essentially light mercaptans such as methyl, ethyl, propyl or butyl mercaptan, as well as their isomers and substituted derivatives, or a compound such as tetrahydrothiophene (THT) which may also be added as an odorizing agent. In the case of a gasoline, the sulphur-containing compounds could be linear, branched or cyclic mercaptans comprising 4 to 10 carbon atoms, for example, as well as aromatic sulphur-containing compounds such as thiophene and its mono- or di-methylated derivatives, or benzothiophene and its mono- or di-methylated derivatives. In the case of a gas oil, the sulphur-containing compounds are essentially aromatic compounds such as benzothiophene and its mono- or di-methylated derivatives, and dibenzothiophene and its mono- or di-methylated derivatives, in particular 4,6-dimethyldibenzothiophene.

The desulphurization operation is preferably carried out in the gas phase. In a variation, it may be carried out in the liquid phase. This is the case when the reaction temperature is lower than the critical temperature of the alcohol and hydrogen mixture.

The capture mass of the invention captures the sulphur-containing organic molecules, in particular molecules considered to be refractory to conventional hydrodesulphurization operations, such as alkylated benzo- or dibenzo-thiophenes.

The zinc ferrite type mixed oxide is generally obtained by co-precipitation followed by calcining. The preparation process does not necessitate an intermediate step for impregnation of a second phase acting as the promoter. The zinc ferrite mixed oxygen is active even with specific surface areas of less than 10 m²/g. The synthesis of the invention of an active mass based on zinc ferrite does not necessitate a sophisticated protocol aimed at developing a large specific surface area required for high reactivity of this solid as regards sulphur-containing molecules. The preparation process does not necessitate a reduction step in order to render the oxide active nor does it require a step for dispersion of the promoter (for example an iron or copper oxide) over the oxide. The reduction step, for example in hydrogen, is generally difficult to carry out on an industrial scale in a fixed bed because of the exothermic nature of the reaction.

However, a prior step for reduction in hydrogen also falls within the scope of the invention. Typical conditions for this step would, for example, be a temperature in the range 300° C. to 400° C., and a pressure which is, for example, in the range from 1 atmosphere to 10 bar.

The process for preparing a mixed zinc ferrite type oxide generally comprises:

a step for co-precipitation of a mixture of zinc II and iron III precursor salts in the presence of a base at a pH in the range of 6.1 to 6.9 and at a temperature in the range of 30° C. to 50° C.;

a step for filtration of the precipitate obtained;

a step for drying the resultant precipitate for a period in the of range 12 to 24 hours, at a temperature in the range of 125° C. to 175° C.;

a step for calcining the dried precipitate in the presence of oxygen at a temperature in the range of 600° C. to 700° C., for a period in the range of 1 hour to 3 hours.

The solid proposed in this invention does not necessitate a step for prior activation by hydrogen in order to be active.

In a variation, the zinc ferrite may be deposited on a support, such as alumina, for example.

The alumina content is thus preferably less than 80% by weight. In another aspect of the invention, the zinc ferrite is not associated with alumina which would otherwise lower the dynamic sulfur capacity of the absorbent containing the zinc ferrite.

The zinc ferrite with formula $ZnFe_2O_4$ generally has a franklinite type crystalline structure.

The zinc ferrite crystallite size is generally in the range 20 Å to 5000 Å, preferably in the range 100 Å to 1000 Å.

The specific surface area of the zinc ferrite, measured using the 77K nitrogen adsorption technique in accordance with the BET method, is generally in the range 2 $m^2/g$ to 10 $m^2/g$. The zinc ferrite is active for specific surface areas of less than 10 $m^2/g$. The zinc ferrite could be used in the form of a powder, beads, or extrudates. The zinc ferrite is preferably operated in a fixed bed but it is also possible to operate using a moving bed.

The micro and mesoporous volume of the zinc ferrite, determined by the same nitrogen adsorption technique using the BJH method or a variation thereof, for example, is less than 0.15 $cm^3/g$.

The macroporous volume of the zinc ferrite, measured using the mercury intrusion and extrusion technique, which is also well known to the skilled person, is less than 0.025 $cm^3/g$.

These characterization techniques have been described, for example, in the work by S Lowell et al, "Characterization of Porous Solids and Powders: Surface Area, Pore Size and Density", Kluver Academic Publishers, 2004.

EXAMPLES

Example No 1

Preparation of a Zinc Ferrite Type Solid Adsorbant

The adsorbant was prepared by precipitation of a mixture of aqueous solutions of zinc (II) nitrate, iron (III) nitrate and an aqueous solution of ammonia as the basifying agent. In the nitrate solution, the concentrations by weight of zinc and iron were respectively 13 g/l and 22.5 g/l. The concentration by weight of precipitation agent was 225 g/l.

At the start of the synthesis, a water starter was introduced into a jacketed borosilicate glass reactor then heated to 40° C., at a stifling power of approximately 150 W/$m^3$ supplied by a propeller-type rotor. The precursors and the base were then introduced into the reactor via a pumping system in order to regulate the rates of introduction and the duration of synthesis. The pH was controlled by the flow rate of the basic pump: it was kept constant at 6.5±0.2 throughout the co-precipitation.

During the reaction, a stifling power of approximately 75 W/$m^3$ was applied to the reaction medium and a temperature of 40° C.±2° C. was maintained in the reactor using a thermostatted bath.

At the end of synthesis, the precipitate was hot filtered through a Buchner flask. The moist cake obtained after filtering for 45 minutes was oven dried for 18 h at a temperature of 150° C. The solid obtained was then calcined in the presence of molecular oxygen at a temperature of 650° C. for 2 h.

The solid obtained was characterized by X ray diffraction using a Bragg-Brentano type powder diffractometer in θ-θ configuration. The recording conditions were as follows: the anticathode tension was adjusted to 35 kV, the intensity in the anticathode filament was fixed at 35 mA, the sampling interval was 0.05° 2θ, the count time per interval was fixed at 5s and the angular field was 2 to 72° 2θ. On the experimental diffractogram obtained for our solid, the positions of the peaks were similar to those of a known crystallographic structure recorded in the "Powder Diffraction File" database corresponding to Franklinite $ZnFe_2O_4$ (PDF N° 00-022-1012). As an example, the positions of the most deep experimental peaks for our solid were as follows: 29.93° 2θ-35.27° 2θ-56.61° 2θ-62.15° 2θ. For franklinite, they are at 29.92° 2θ-35.26° 2θ-56.63° 2θ-62.21° 2θ. The lattice parameters (a=b=c in the case of a cubic system) were identical, i.e. equal to 8.44 Å. For our solid, the mean zinc ferrite crystallite size was 410±40 Å.

A semi-quantitative analysis using X ray fluorescence was also carried out on our synthesized solid. The contents obtained after correction for a loss on ignition carried out at 550° C., 4 h (LOI=0.3%) resulted in the following contents: wt % Fe=42.48±0.74% and wt % Zn=23.18±0.78%.

Finally, the specific surface area developed by the solid was estimated by low temperature nitrogen volumetry using the standards ASTM D 3363-84 or NFX 11-621; it was equal to 6±1 $m^2/g$.

Example No 2

Desulphurization by chemisorption on zinc ferrite of a model feed of 95% ethanol denatured with 5% hexane and 60 ppmS of butanethiol.

The second example describes the use of a solid in a fixed bed type reactor. 12 grams of solid in the form of a powder produced as described in Example 1 was introduced into a column with a 1 cm internal diameter and with a useful volume of 9 $cm^3$. Depending on the density of the solid, quartz wool and an inert substance with a granulometry equivalent to the test solid were symmetrically added to the reactor. The column was placed in a temperature-regulated oven. Before the test, the solid was initially reduced in a stream of hydrogen (5.7 nL/hr) at high temperature, 380° C., and at a pressure of 7 bar for 12 hours. After cooling, the oven temperature was brought to 250° C.

The temperature adjustment was an external adjustment, with measurements taken of the temperature of the column wall, which meant that operation could be carried out without a thermowell and preferential paths in the column could be avoided.

The discharged effluent was held at temperature and removed using a sampling loop for on-line analytical monitoring. The compounds were analyzed by gas chromatography using FID detection and a PFPD analyzer.

A model liquid feed constituted by ethanol was supplied at a HSV of 4 $h^{-1}$ using a Gilson syringe pump, then vaporized in the presence of hydrogen using a dedicated device, then injected into the reactor. The pressure in the reactor was 9 bar and the hydrogen/feed ratio at the reactor inlet was 420.

As soon as the feed came into contact with the adsorbant, a quasi-immediate drop in the sulphur content in the effluent from the reactor was observed to values of less than 5 ppm by weight. The sulphur profile as a function of time at the reactor outlet then remained constant and at less than 1 mg/l before the phenomenon of breakthrough occurred, which corresponded to a rise in the concentration of sulphur to the value of the sulphur concentration at the inlet when the adsorbant was completely saturated with sulphur. Before breakthrough, no trace of sulphur could be detected by the PFPD detector of the gas chromatograph.

Two parameters representing the performance of the zinc ferrite based solid can be distinguished in the described example:

the dynamic capacity, which corresponds to the quantity of sulphur trapped on the adsorbant just before breakthrough. Under the operational conditions used, the dynamic sulphur capacity of the zinc ferrite based adsorbant was 9% by weight;

the saturation capacity, which corresponds to the maximum sulphur capacity of the adsorbant measured after saturation. Under the operational conditions used, the sulphur saturation capacity of the zinc ferrite based adsorbant was 14% by weight.

The preceding examples can be repeated with similar success by substituting the generically or specifically described reactants and/or operating conditions of this invention for those used in the preceding examples.

The entire disclosures of all applications, patents and publications, cited herein and of corresponding French Application Serial No. 08/05.624, filed Oct. 10, 2008 are incorporated by reference herein.

The invention claimed is:

1. A process for desulphurizing an essentially alcoholic feed comprising at least one of methanol and/or ethanol in 1 to 10% by weight of a denaturing agent, comprising at least one hydrocarbon containing compound and at least one organic sulphur-containing compound based on the weight of the alcoholic feed, said process comprising capturing sulfur in a capture mass comprising more than 20% by weight of zinc ferrite of the formula $ZnFe_2O_4$ said capture mass being produced by:

a step for co-precipitation of a mixture of zinc II and iron III precursor salts in the presence of a base at a pH in the range of 6.1 to 6.9 and at a temperature in the range of 30° C. to 50° C.;

a step for filtration of the precipitate obtained;

a step for drying the resultant precipitate for a period in the of range 12 to 24 hours, at a temperature in the range of 125° C. to 175° C.;

a step for calcining the dried precipitate in the presence of oxygen at a temperature in the range of 600° C. to 700° C., for a period in the range of 1 hour to 3 hours said desulphurizing process comprising passing said feed over said capture mass in the presence of hydrogen at a temperature in the range of 200° C. to 400° C.

2. A process according to claim 1, conducted at a pressure in the range of 0.2 to 3.5 MPa.

3. A process according to claim 1, conducted at a pressure in the range of 0.5 to 3 MPa.

4. A process according to claim 1, conducted with an hourly space velocity of the feed to be treated in the range of $0.1\ h^{-1}$ to $10\ h^{-1}$.

5. A process according to claim 1, conducted with a hydrogen/feed volumetric ratio in the range of 5 to 500.

6. A process according to claim 5, wherein the volumetric ratio is in the range of 50 to 300.

7. A process according to claim 1, in which the feed comprises aliphatic, cyclic and/or aromatic sulphur-containing compounds.

8. A process according to claim 1, in which the capture mass comprises more than 80% by weight of zinc ferrite.

9. A process according to claim 1, in which the capture mass comprises more than 98% by weight of zinc ferrite.

10. A process according to claim 1, wherein the organic sulphur-containing compounds comprise alkylated benzo- or dibenzo-thiophenes.

11. A process according to claim 1, wherein the resultant zinc ferrite is deposited on alumina.

12. A process according to claim 1, wherein the alcohol consists essentially of methanol.

13. A process according to claim 1, wherein the process for preparing the zinc ferrite is devoid of a reduction step with a reducing agent.

14. A process according to claim 1, wherein the zinc ferrite is not subjected to prior activation with hydrogen in order to be active.

15. A process according to claim 1, wherein the base is ammonia.

16. A process according to claim 1, wherein the content of the denaturing agent is about 1% to 5% by weight.

* * * * *